US005583335A

United States Patent [19]
Spitzer et al.

[11] Patent Number: 5,583,335
[45] Date of Patent: Dec. 10, 1996

[54] METHOD OF MAKING AN EYE TRACKING SYSTEM HAVING AN ACTIVE MATRIX DISPLAY

[75] Inventors: Mark B. Spitzer, Sharon, Mass.; Jeffrey Jacobsen, Hollister, Calif.

[73] Assignee: Kopin Corporation, Taunton, Mass.

[21] Appl. No.: 395,180

[22] Filed: Feb. 27, 1995

Related U.S. Application Data

[63] Continuation of Ser. No. 275,777, Jul. 15, 1994, abandoned, which is a continuation of Ser. No. 985,285, Dec. 4, 1992, Pat. No. 5,331,149, which is a continuation-in-part of Ser. No. 851,178, Mar. 13, 1992, abandoned, which is a continuation-in-part of Ser. No. 643,552, Jan. 18, 1991, Pat. No. 5,300,788, and Ser. No. 636,602, Dec. 31, 1990, Pat. No. 5,206,749, and Ser. No. 834,849, Feb. 13, 1992, Pat. No. 5,258,325, and Ser. No. 815,684, Dec. 31, 1991, Pat. No. 5,317,236.

[51] Int. Cl.⁶ .................................................. G01V 9/04
[52] U.S. Cl. ................................... 250/221; 345/7
[58] Field of Search ............................ 250/221, 561, 250/214.1, 208.1, 208.2, 214 R; 345/7-9; 359/630, 368, 87; 358/109, 107, 113, 236

[56] References Cited

U.S. PATENT DOCUMENTS

| 3,375,375 | 3/1968 | Abbey et al. | 250/216 |
|---|---|---|---|
| 3,967,253 | 6/1976 | Tsuruishi | 340/173 |
| 4,028,725 | 6/1977 | Lewis | 358/103 |
| 4,034,401 | 7/1977 | Mann | 358/93 |
| 4,109,145 | 8/1978 | Graf | 250/201 |
| 4,181,405 | 1/1980 | Cohen | 350/174 |
| 4,231,640 | 11/1980 | Funada et al. | 359/87 |
| 4,287,809 | 9/1981 | Egli et al. | 89/41 |
| 4,361,384 | 11/1982 | Bosserman | 350/174 |
| 4,568,159 | 2/1986 | Baldwin | 351/209 |
| 4,636,866 | 1/1987 | Hattori | 358/236 |
| 4,852,988 | 8/1989 | Velez et al. | 351/210 |
| 4,884,219 | 11/1989 | Waldren | 364/514 |
| 5,093,567 | 3/1992 | Stavely | 250/221 |

FOREIGN PATENT DOCUMENTS

| 0408344A3 | 1/1991 | European Pat. Off. |
| 2522804 | 9/1983 | France . |
| 2612351 | 9/1988 | France . |
| 2715446 | 10/1978 | Germany . |
| 54-93378 | 7/1979 | Japan . |
| 60-46019 | 3/1985 | Japan . |
| 1-259580 | 10/1989 | Japan . |
| WO91/04508 | 4/1991 | WIPO . |

OTHER PUBLICATIONS

Katz, Warren, "Low Cost Helmet Mounted Display and Eye Tracking Concepts," Mak Technologies, Inc. May 15, 1991.
Dutta et al, "A Novel Binarily Detectable High–Speed Optical Position–Sensitive Device (BPSD)", *Journal of Lightwave Technology*, 10(3):391–395, (Mar. 1992).
Matsuda, Tetsuro, "The LCD Challenge to Cathode Ray Tubes," *JEE*, pp. 57–58, 60–61, (Aug. 15, 1988).
Ahrenkiel et al., "Minority–carrier Lifetime in GaAs Thin Films," *Apl. Phys. Lett* 53(7), pp. 598–599 (Aug. 15, 1988).

*Primary Examiner*—Que Tan Le
*Attorney, Agent, or Firm*—Hamilton, Brook, Smith & Reynolds, P.C.

[57] ABSTRACT

An eye tracking system is disclosed which is comprised of an eye tracking module formed of a display joined to a photodetector array. Each pixel in the display is aligned with a corresponding photodetector. An image generated by the display is projected onto a viewing screen or toward a viewer. Axial light rays from the display pixels are reflected by the eye and detected by a respective photodetector which generates an electrical signal indicative of eye position.

20 Claims, 6 Drawing Sheets

METHOD OF MAKING AN EYE TRACKING SYSTEM HAVING AN ACTIVE MATRIX DISPLAY

RELATED APPLICATIONS

This application is a continuation of application Ser. No. 08/275,777 filed Jul. 15, 1994, now abandoned, which is a continuation of Ser. No. 07/985,285 filed Dec. 4, 1992, now U.S. Pat. No. 5,331,169, which is a continuation-in-part of Ser. No. 07/851,178 filed Mar. 13, 1992, now abandoned, which is a continuation-in-part of Ser. No. 07/643,552 filed Jan. 18, 1991 now U.S. Pat. No. 5,200,789, and of Ser. No. 07/636,602 filed Dec. 31, 1990 now U.S. Pat. No. 5,206,749, and Ser. No. 07/834,849 filed Feb. 13, 1992, now U.S. Pat. No. 5,258,325, and Ser. No. 07/815,684 filed Dec. 31, 1991, now U.S. Pat. No. 5,317,236. All of the above applications are incorporated herein by reference in their entirety.

BACKGROUND OF THE INVENTION

Eye tracking systems are useful in flight control, flight simulation and virtual imaging displays. Eye control systems generate information based on the position of the eye with respect to an image on a display. This information is useful for a variety of applications. It can be used to enable the viewer to control "hands-free" movement of a cursor, such as a cross-hair on the display.

Apparatus for detecting the orientation of the eye or determining its line-of-sight (LOS) are called occulometers or eye trackers and are well known in the art. (See for example U.S. Pat. Nos. 4,109,145, 4,034,401 and 4,028,725).

SUMMARY OF THE INVENTION

In accordance with the present invention a detector array comprising thin film integrated optical diode detectors is formed of III–V materials and transferred directly onto a flat panel active matrix display. The display is preferably either an electroluminescent (EL) or an active matrix liquid crystal display (AMLCD) comprised of thin film transistor driving elements formed of single crystal silicon and then transferred to a transparent glass substrate. The TFT is connected to an electrode which defines a picture element (pixel) of the display.

The detectors are positioned such that each is completely above the drive transistors of the active matrix circuit i.e., adjacent to the pixel area and therefore do not block any of the display's light output. The light output from the display, either infrared or visible, is used to determine the position of the eye. No additional optics, such as, fiber optics to/from remote displays are required in this approach. The chief advantage is that the integrated eyetracker/display can be inserted in a helmet-mounted optical system without physical modification to the helmet or optics. This advantage results from the fundamental reciprocity of the axial light rays that are used to determine the eye position. An axial ray, is a light ray that emanates from the display and travels through the optical axis of the eye, normal to the retina. These rays, when reflected by the retina, travel back to the display along the same optical path (by the optical reciprocity theorem). Except for divergence of the rays, the reflected rays return to the vicinity of the emitting pixel. In this way, the detector can identify the area of the display that is sighted by the user. Software in a computer then provides a cursor at this location.

In another alternative embodiment; instead of using the visible scene from the display, some of the frames in the display are used for brief presentation of an interlaced eyetracker pattern. If the repetition rate of the test pattern is sufficiently infrequent, the user (viewer) will not perceive its presence. This pattern may consist of a single pixel being illuminated or may have some other geometric pattern. Light from a single lit pixel enters the eye through the pupil and is reflected from the retina. The path of the reflected light clearly depends on the position of the eye. On the reverse path back to the display panel, the reflected light undergoes spreading or convergence depending upon the optical system. As it returns to the plane of the display, it strikes the photodetectors. A pattern will appear in the output of the photodetector array that depends on the position of the eye and the nature of the optical system. This pattern is interpreted by a computer and correlated to the position of the eye.

DETAILED DESCRIPTION OF THE INVENTION

Figure 1:
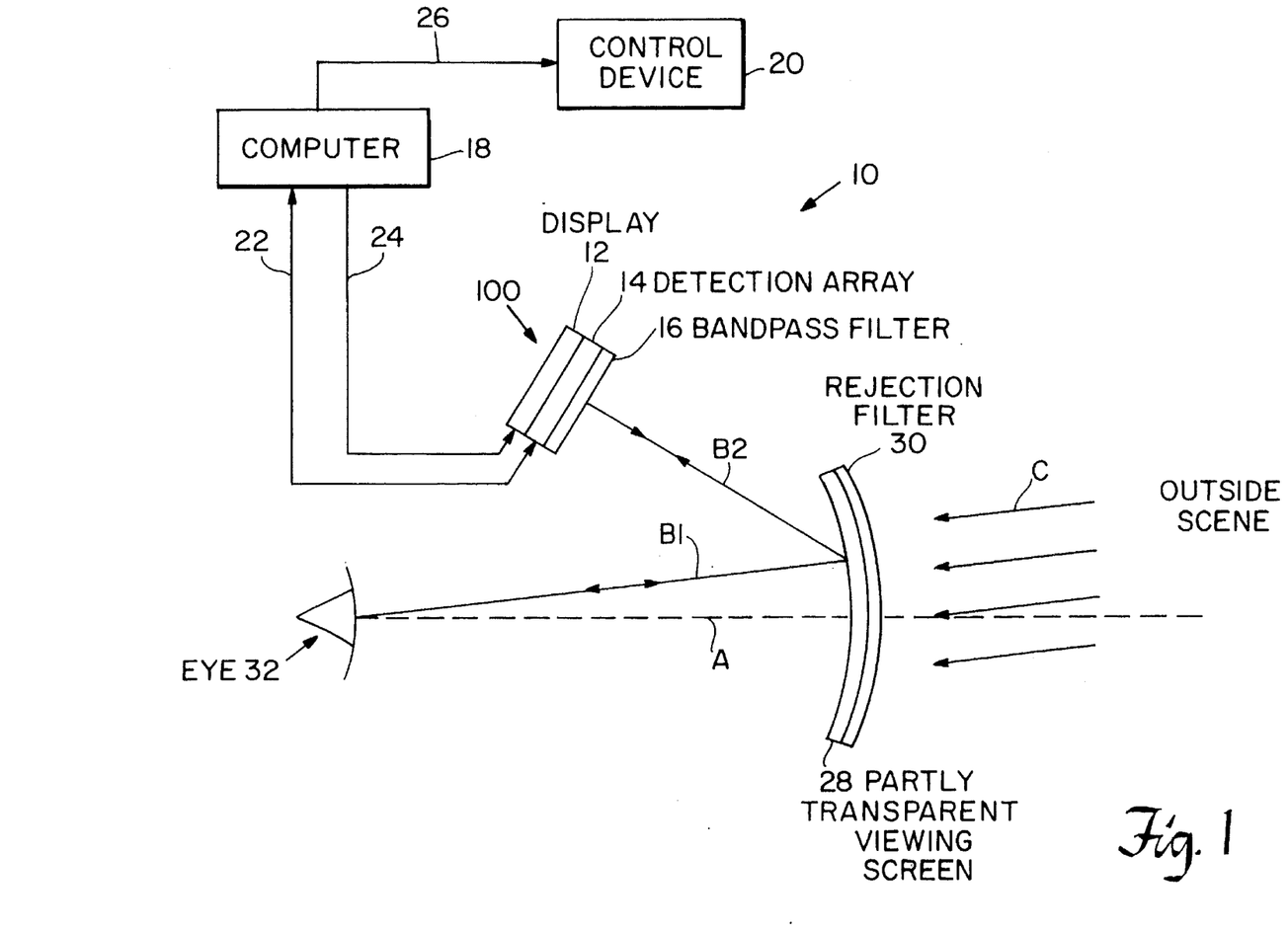
FIG. 1 is a schematic diagram of an eye tracking system of the invention.

Referring now to the schematic diagram of FIG. 1, it may be seen that the present invention relates to an eye tracking system 10 that combines a flat panel display device 12 with an array of optical detectors 14 to form an eye tracker device 100. The flat panel display device is used as a monolithic substrate and light source for determining the position of the eye 32. The detector array 14 is aligned and transferred onto the active matrix electronics of the flat panel device. A test pattern and software in computer 18 analyzes the sensed data generated by the detector on display and determines the position of the eye.

Light from display 12 is used to project an image onto viewing screen 28 for viewing by the eye(s) 32 of a viewer. The image to be displayed is generated in computer 18 and is coupled as an electrical input video signal to display 12 along line 24. Image light rays from display 12 pass through detector array 14 and are projected onto screen 28 where they may be superimposed on external images from an outside scene formed by light rays C.

A light ray emanating from a particular pixel of display 12 is shown as line B2. This ray is reflected by the screen 28 (line B1) onto the eye optics (not shown) and on to the macula (not shown) of eye 32. The axial rays of greatest importance will impinge on the fovea of the eye, the most sensitive part of the macula. These rays return to the display in the vicinity of the original pixel because reflection from the fovea is approximately normal to the retina and therefore nearly axial. Non-axial rays which will impinge on the retina beyond the fovea will not be reflected back along the axial optical path and will not return to the detector array 14.

The viewing screen 28 may comprise, for example, the visor of a heads-up helmet mounted optical system for pilots and the integrated detector/display can be inserted in a helmet-mounted optical system without physical modification to the helmet or optics. Additionally, no physical contact with the eye is required.

Once the axial rays B1, B2 return to the display, the detector array 14 identifies the portion of the array from which the axial ray emanated, by generating a voltage signal by a detector pixel located in the array nearest the returned ray. That portion of the array is, of course, the part of the display focussed on by the user. A test pattern from computer 18 is then interlaced with the display image to enable initial determination of the eye's position. Software, in computer 18, provides a cursor image for display 12 which is projected on screen 28 at the line-of-sight location. This cursor is interlaced to provide constant feedback to the detector array 14. The interlace frequency can be adjusted to make the cursor visible or not visible to the user.

Figure 2:
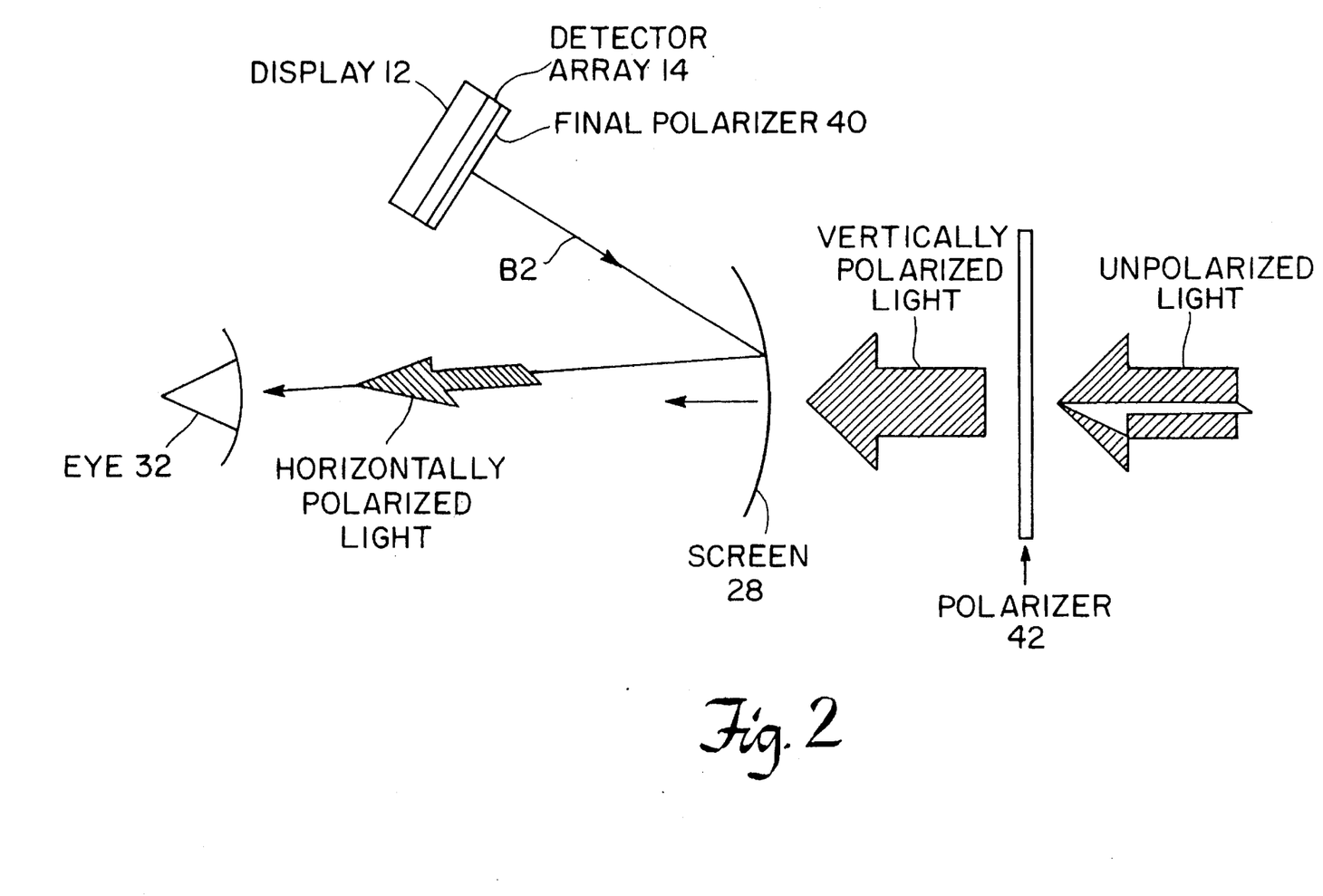
FIG. 2 is a schematic of an alternate embodiment of an eye tracking system of the invention.

For the case of a partially transparent system of FIG. 1 in which scenes from the surroundings are superimposed on the display image, the detector array 14 is provided with a narrow band pass filter overlay to reject all wavelengths except the wavelength of the cross hair or cursor, which must be one of the display primary colors. Suppose for example that the selected color is primary red. In this case, a narrow band red rejection filter 30 is placed on the outside of the screen 28, and a narrow red bandpass filter 16 is placed over the pixels of the detector array 14. In this way, the detector array 14 only receives light originating from the display. A second method of accomplishing the same result is to use polarizing filters as shown in FIG. 2. In this case the flat panel display 12 is an AMLCD light valve helmet or head mounted display (HMD), having a polarizer 40 on its output face. The polarized nature of the light from the display 40, combined with a 90° crossed polarizer 42 on the screen 28, prevents unwanted light from the outside scene from propagating to the detector array.

Another alternative is to chop or rapidly blink the video signals from computer 18 for the cursor presentation so that software in the computer can subtract the background light. Yet, another alternative that can be used with LCD displays is to use infrared light that can pass through the red filters of the LCD. But this approach requires an IR rejection filter on the front of the viewing screen. It can be seen from the above that there are a number of methods of using the display 12 to provide a signal for the detector array 14, without interference from outside light.

Figure 3:
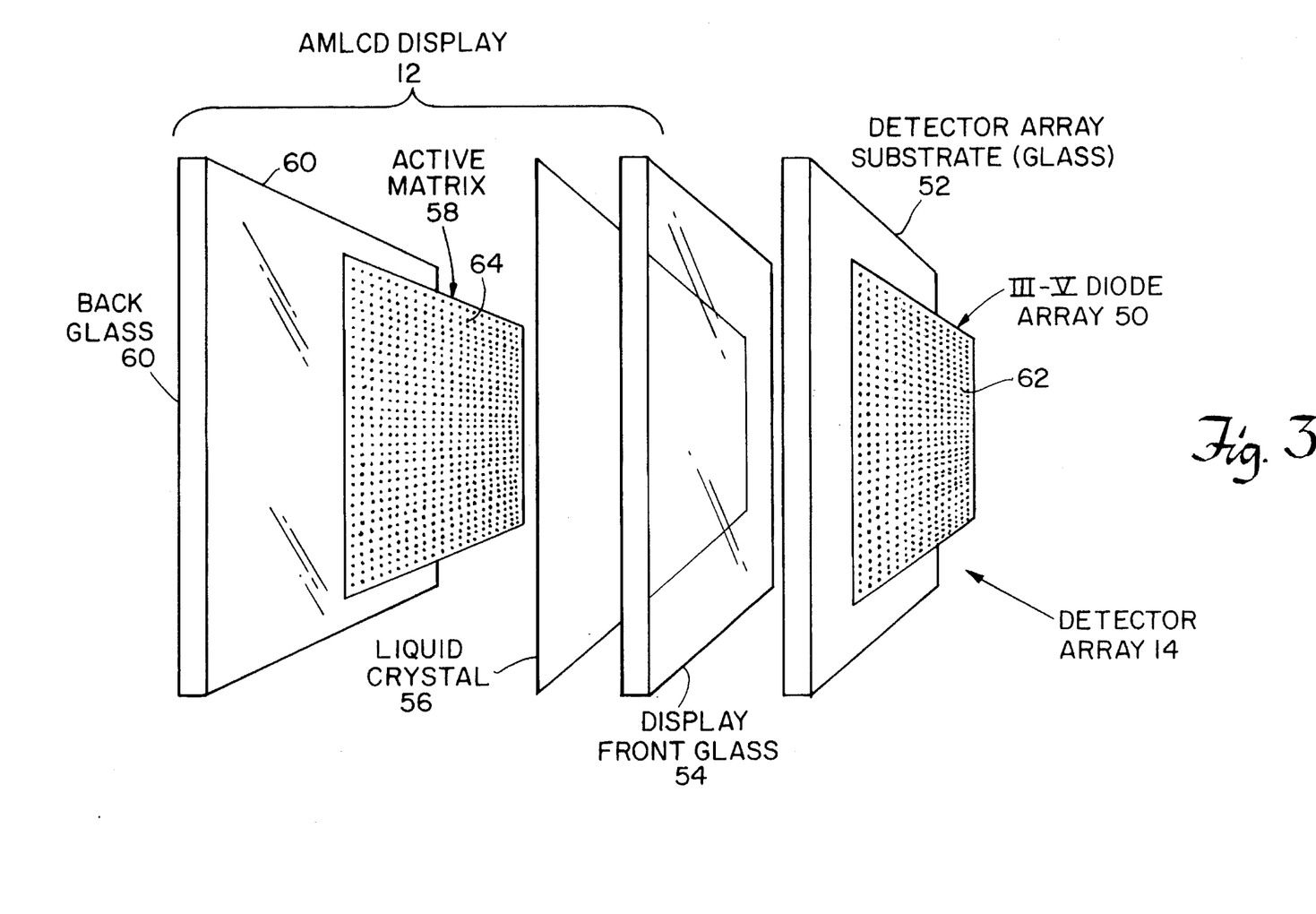
FIG. 3 is an exploded view of the integrated display/detector array panel (eye-tracker) of the invention.

An exploded view of an AMLCD display and monolithic detector array 14 in accordance with the invention is illustrated in FIG. 3. Note that a complete eye-tracker package can be made without substantially changing the overall dimensions of the display. As shown in FIG. 3, a detector array 14 is formed of a III–V diode array 50 transferred to a glass substrate 52 or directly above and onto front glass 54 of an active matrix LCD display 12. The detector pixels 62 are positioned so that each is completely above the drive transistors 64 of the active matrix circuit and therefore do not block any of the display's light output from pixel electrodes 64. (See FIG. 4). The detector row and column interconnects (not shown) are positioned directly above the display row and columns, so that the interconnect wires do not block any light.

Figure 4:
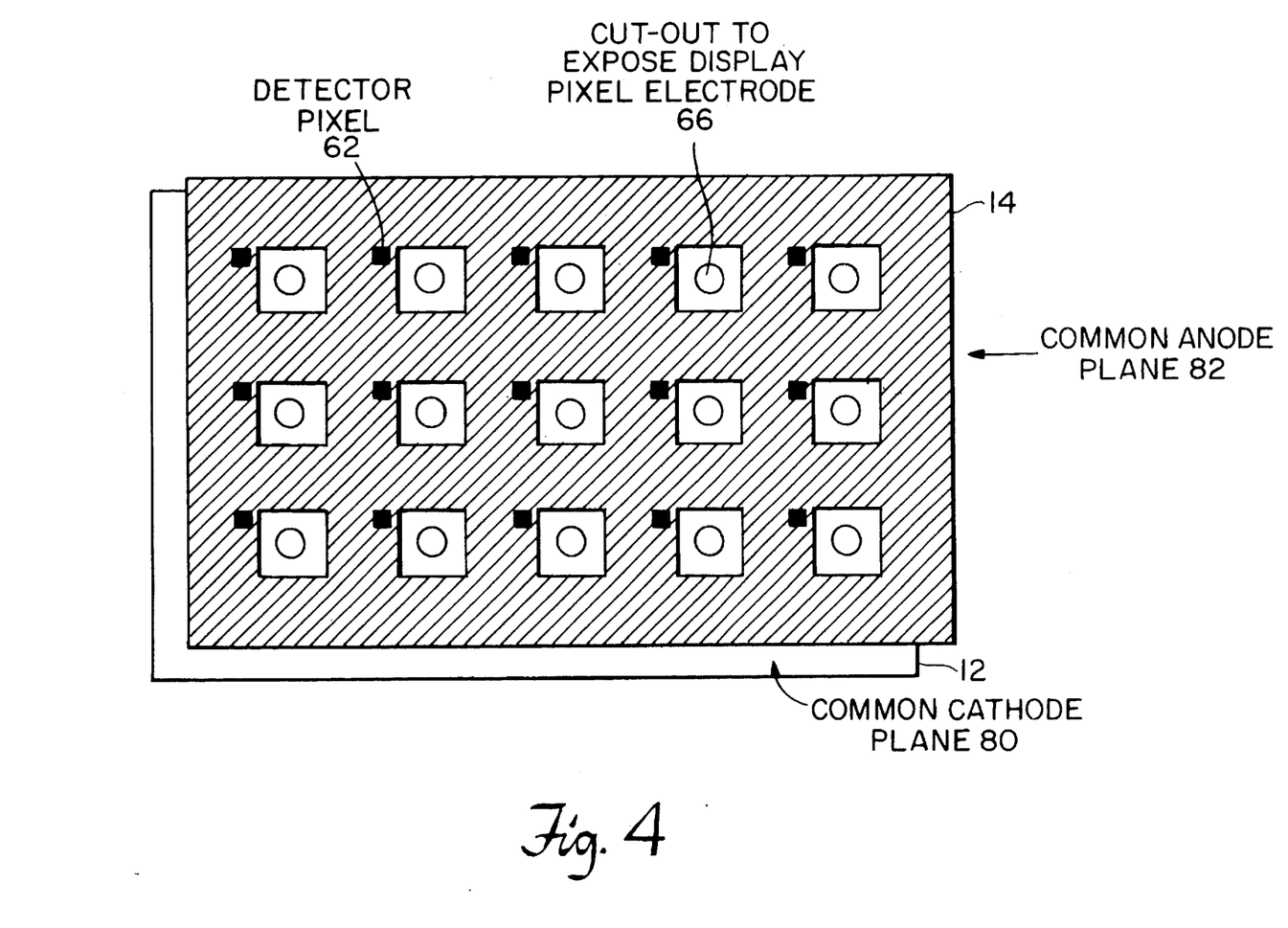
FIG. 4 is a plan view of a simplified version of the eye tracker in which the matrix array metallization is replaced by a common parallel interconnect.

Note that the cut-out shown in FIG. 4 is not required in practice since the detector array substrate 52 is made of transparent material such as glass or quartz.

For infrared detection, GaAs appears to be the best choice for the detector elements. The bandgap of GaAs is 1.43 eV, corresponding to an absorption edge of about 0.87 µm. This material may also be suitable for visible light; however, if it is desirable to suppress infrared absorption in the detector, the bandgap can be increased to about 1.9 eV (0.65 µm) by adding aluminum (Al) to form the ternary compound semiconductor $Al_xGa_{x-1}As$. (A bandgap of 1.9 eV is obtained for x=0.38.)

Figure 5A:
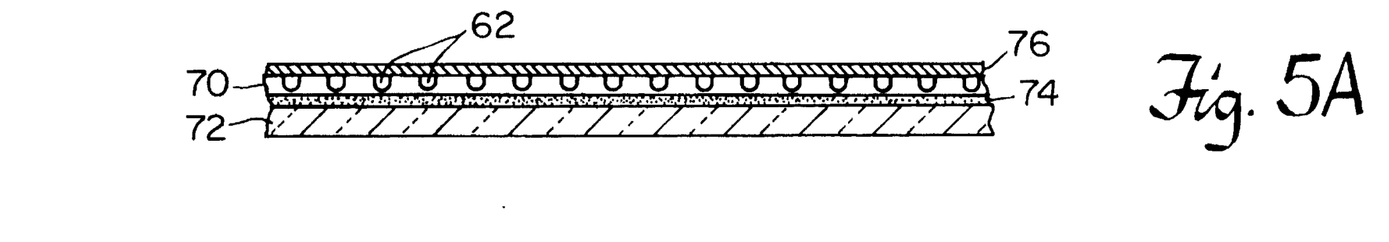
FIGS. 5A–5C are cross-sectioned views showing important steps in the process of forming the eye-tracker device of the invention.
Figure 5B:
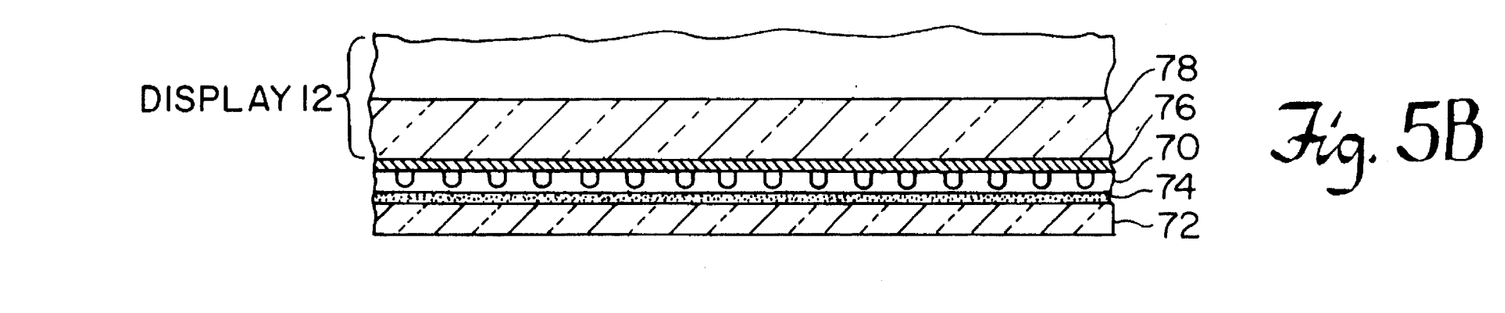
Figure 5C:
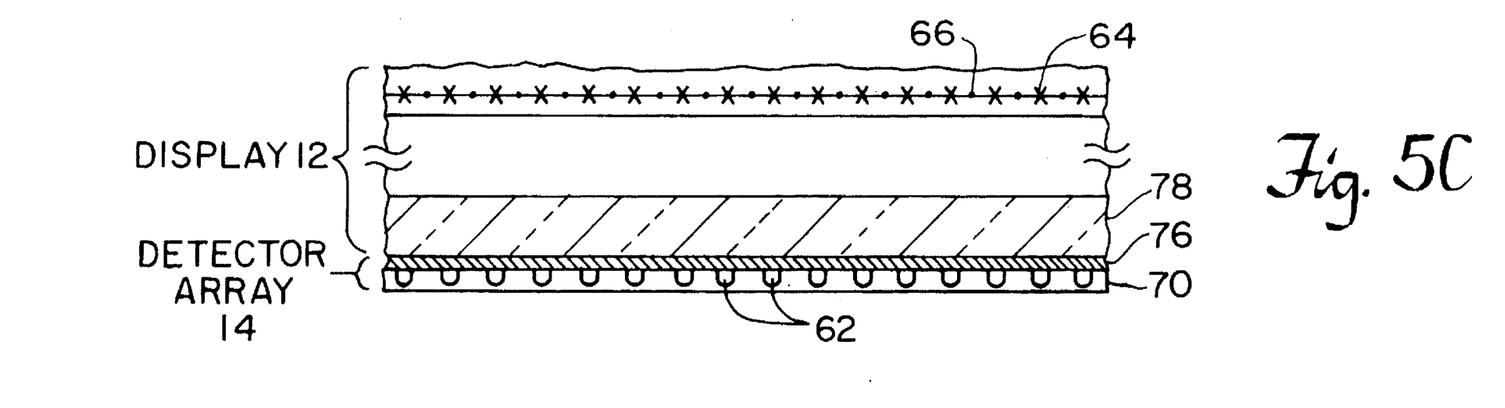

The process used to form the detector array is based on the LED array process described in the above-referenced co-pending application Ser. No. 07/643,552, as a baseline. In this process, the detector material 70 is first grown on substrate 72 by OMCVD. A release layer 74 is formed that permits the epitaxial film 70 to be separated from the substrate 72, but separation is deferred until after the front side metallization 76 is formed (FIG. 5A). After metallization of rows of metallization and mesa etching to delineate the pixels 62, the surface of the wafer is bonded to a carrier 78 (FIG. 5B). This carrier is preferably the front panel 54 of display 12. The substrate 72 is then removed to yield a partially processed detector array 14 bonded to a display array 12. The processing is then completed to form a matrix addressed two-dimensional array 12 of detector pixels 62 aligned with the TFT's 64 (indicated by X's) but slightly displaced from corresponding pixel electrodes 66 (indicated by dots) of the display array 12 (FIG. 5C).

Several points need to be emphasized regarding the formation of the integrated detector array 14 and display 12. First, the matrix metallization (not shown) of the detector must be positioned over the metallization of the display. In this way, no decrease in the optical aperture of the display is introduced by the metal interconnects of the detector array 14. Second, the detector pixels 62 can be made as small as a few microns square provided the detector sensitivity is high enough. Since the TFT's are also in the order of a few microns wide, detector pixels of such size would not block light. Third, the detector array 14 does not need to use an active matrix, because III–IV materials, such as, GaAs and AlGaAs are extremely fast detectors (<1 µs decay time) and so the detector array can be scanned as fast or faster than the display. Since the detector pixels are small, they can be placed over the transistors in the active matrix display, resulting in very little reduction in optical aperture of the display.

The integrated eyetracker device 100 can consist of a pair of units that can be simultaneously scanned by computer 18 to obtain real time correlation between the probe or cursor signal and the detected LOS signal. This real-time signal correlation can be used to eliminate the complicated image processing software that is ordinarily needed to analyze a CCD dark pupil image.

The line-of-sight information obtained may be processed in computer 18 and coupled to control device 20 along line 22 to execute functions, or to display 12 along line 24 to present various images or for generating a high resolution image only in the line-of-sight vicinity.

The detector array may alternatively be mounted on the back panel of the display 12 or preferably integrated with the formation of the display array. In this integrated embodiment, the detector pixels are formed of Si on the TFT substrate in the same process in which the TFT's are formed. Each detector pixel is located adjacent a corresponding TFT pixel.

The display array may be comprised of an EL panel formed as illustrated in FIG. 16A of U.S. Ser. No. 07/815,684 commencing on page 41 and referenced above. In this case, the detector array would be transferred to the EL panel 419 of the referenced application.

The eye tracking device of the invention offers numerous system simplifications. One simplification is made possible by the use of the high speed III–V detector array 14. Scanning of the array can be synchronized with the display scan. This eliminates the complex software needed for pattern recognition in the typical CCD approach. This is because the reflected light can be analyzed pixel-by-pixel in real time to determine the area on which the viewer is focusing. Moreover, depending on the angular resolution needed, it may be possible to replace the detector matrix array with a much simpler array of pixels interconnected in a common parallel circuit, as shown in FIG. 4 comprising anode plane 82 and cathode plane 80. Only two terminals are used for connection to the detector plane 82. Light reflection from the non-macular portion of the retina largely falls beyond the detector array 14 and macular reflection returns to some location on the array 14. The display 13 is scanned row by row while the computer simultaneously monitors the reflected signal at the detector. The row yielding the highest signal is the row upon which the viewer is focused. A similar scan is performed for the columns to determine the column pixels upon which the viewer is focused.

Figure 6:
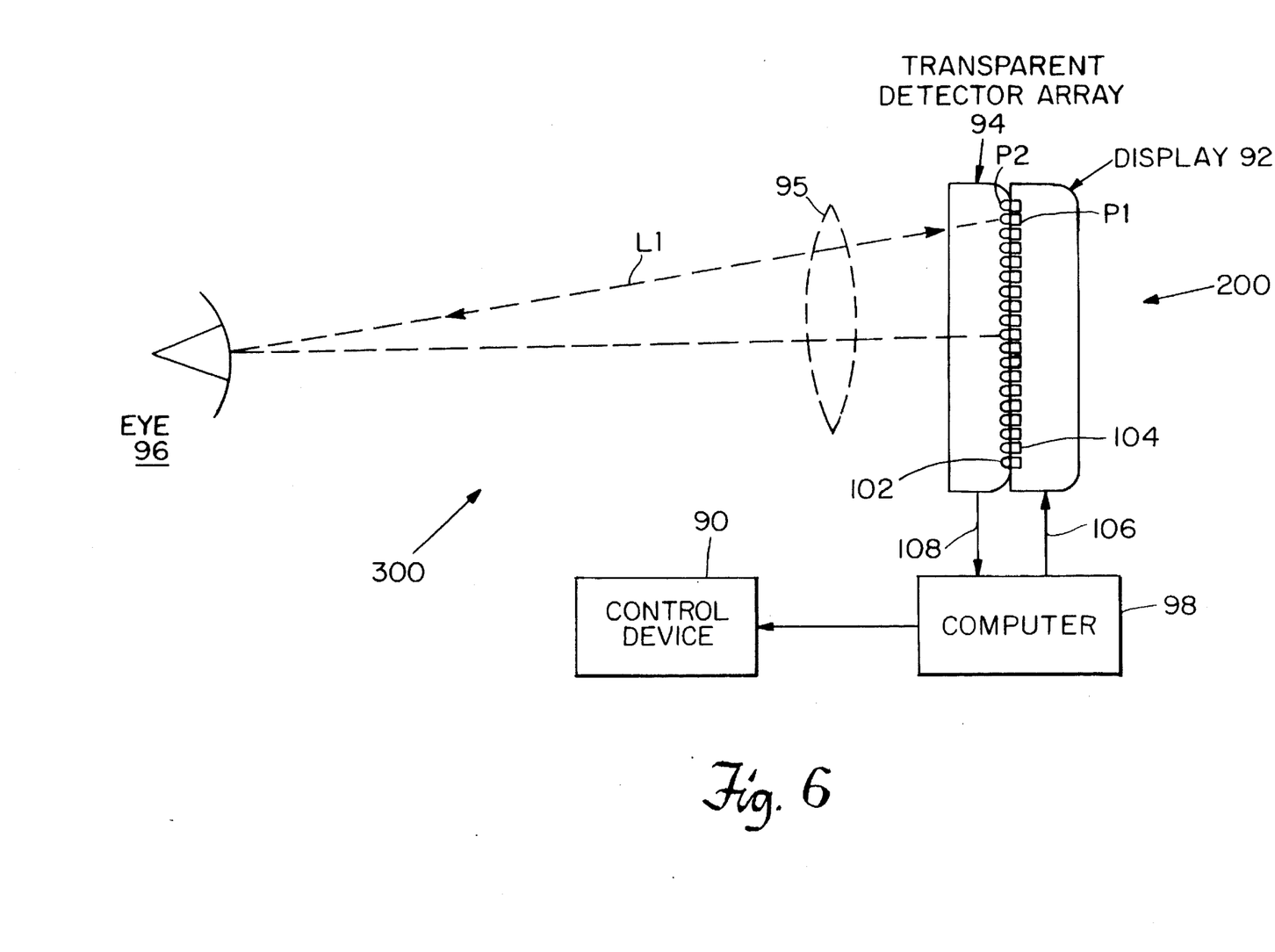
FIG. 6 is a schematic diagram of an alternate embodiment of an eye tracking device of the invention.

Referring now to the schematic diagram of FIG. 6, an alternate embodiment of the present invention will now be described. This embodiment relates to a direct viewing eye tracking system 300 that combines a flat panel display device 92 with a substantially transparent array of optical detectors 94 to form an eye tracker device 200. As in FIG. 1, flat panel display device 92 is used as a monolithic substrate for the detector array and as a light source for determining the position of the eye 96. The detector array 94 and display 92 are preferably formed as in FIGS. 3 and 5 or in any of the related patent applications. The array is aligned and transferred onto the active matrix electronics of the flat panel display 92. A test pattern and software in computer 98 analyzes the sensed data generated by the individual detectors 102 of the array 94 and determines the position of the eye based upon which detector(s) senses light reflected from the eye.

Light from display 92 is used to project an image for viewing by the eye(s) 92 of a viewer. The image to be displayed is generated in computer 98 and is coupled as an electrical input video signal to display 92 along line 106. Image light rays from display 92 pass through detector array 94 and are viewed by the eye 96.

A light ray emanating from a particular pixel P1 of display 92 is shown as line L1. This ray impinges on the fovea of the eye 96 and is reflected back along line L1. The ray returns to the display 92 in the vicinity of the original pixel because reflection from the fovea is approximately normal to the retina and therefore nearly axial. Non-axial rays which impinge on the retina beyond the fovea will not be reflected back along the axial optical path.

Once the axial ray L1 returns to the display 92, the detector array 94 identifies the portion of the array at which the axial ray returns by generating a voltage signal from a detector pixel P2 located in the array nearest the returned ray. That portion of the array is, of course, the part of the display focussed upon by the eye 96 of the user. This voltage signal, indicative of eye position, is coupled on line 108 to computer 98. A test pattern from computer 98 is then generated by computer 18 and interlaced with the display image to indicate to the user the eye's position. Software, in computer 18, provides a test pattern in the form of cursor image on display 92 which is formed at the line-of-sight location. The cursor is interlaced to provide constant feedback to the detector array 94. The interlace frequency can be adjusted to make the cursor visible or not visible to the user. An optional lens system 95 may be employed between the eye and array to enhance the image projected from the display 92. The line-of-sight information obtained in array 94 may be processed in computer 98 and coupled to control device 90 to execute functions or may be coupled to present various images, such as, the previously mentioned cursor.

The preceding description is particular to the preferred embodiments and may be changed or modified without substantially changing the nature of the invention. For example, while the invention has been illustrated primarily by use of a passive substantially transparent LCD display, other type displays both active and passive are within the contemplation of the invention; such as, without limitation, the following: active displays, e/g. plasma display panels, electroluminescent displays, vacuum fluorescent displays and light emitting diode displays; passive displays: electrophoretic image displays, suspended particle displays, twisting ball displays or transparent ceramic displays. In each case the photodetector would be formed in the same film as the display pixel or monolithically formed above or below the pixel to sense which pixel or group of pixels receive eye reflected light. While the invention has been particularly shown and described with reference to preferred embodiments thereof, it will be understood by those skilled in the art that various changes in form and details may be made therein without departing from the spirit and scope of the invention as defined by the appended claims.

We claim:

1. A method of fabricating a device for detecting the line-of-sight position of the eye of a viewer comprising:

forming an active matrix display over a substrate;

forming a detector array;

mounting the detector array onto the active matrix display and the substrate to form an eye tracking device, the detector array mounted such that an image generated by the active matrix display can be seen by the viewer; and mounting the eye tracking device on a head-mountable structure.

2. The method of claim 1 wherein the step of forming the active matrix display further comprises forming an array of circuit elements in a silicon material.

3. The method of claim 1 wherein the active matrix display comprises a liquid crystal display or a light emitting display.

4. The method of claim 1 wherein the detector array is monolithically fabricated over the active matrix display.

5. The method of claim 1 further comprising the step of aligning the detector array with the active matrix display.

6. The method of claim 1 further comprising forming a filter over the detector array.

7. The method of claim 1 wherein the detector array comprises a charge coupled device.

8. The method of claim 1 further comprising forming the active matrix with a silicon layer and transferring the active matrix onto the substrate.

9. The method of claim 1 wherein the step of forming a detector array comprises forming a parallel circuit.

10. A method of forming an eye tracking device comprising:

forming an active matrix display circuit over a substrate;

monolithically forming a detector array over the substrate to provide a display and detector structure;

mounting the display and detector structure in a head mountable device such that the structure can detect a position of a user's eye.

11. The method of claim 10 wherein the step of forming the active matrix display circuit further comprises forming an array of circuit elements in a silicon material.

12. The method of claim 10 wherein the active matrix display comprises a liquid crystal display or a light emitting display.

13. The method of claim 10 further comprising connecting the display and detector to a computer.

14. The method of claim 10 further comprising the step of aligning the detector array and the active matrix display circuit.

15. The method of claim 10 further comprising forming a filter over the detector array.

16. The method of claim 10 wherein the detector array comprises a charge coupled device.

17. The method of claim 10 further comprising forming the active matrix with a silicon layer and transferring the active matrix onto the substrate.

18. The method of claim 10 wherein the step of forming a detector array comprises forming a parallel circuit.

19. A method of fabricating a device for detecting the line-of-sight position of the eye of a viewer comprising:

forming an active matrix display over a substrate;

forming a detector circuit;

mounting the detector circuit over the active matrix display and the substrate to form an eye tracking device, the detector mounted such that an image generated by the active matrix display can be seen by the viewer; and mounting the eye tracking device on a head-mountable structure having an optical system for directing light from the viewer's eye to the detector.

20. The method of claim 19 wherein the optical system comprises a lens or a mirror.

* * * * *